(12) United States Patent
Belcher et al.

(10) Patent No.: US 7,954,392 B2
(45) Date of Patent: Jun. 7, 2011

(54) COATED SUBSTRATE WITH PROPERTIES OF KERATINOUS TISSUE

(75) Inventors: William Randal Belcher, Bellbrook, OH (US); Mannie Lee Clapp, Mason, OH (US); Saswati Datta, Cincinnati, OH (US); Magda El-Nokaly, Cincinnati, OH (US); Sandra Lou Murawski, Fairfield, OH (US); Steven Hardy Page, Lawrenceburg, IN (US); Sohini Paldey, Forest Park, OH (US); Ronald Ray Warner, Cincinnati, OH (US); Raphael Warren, Amberly Village, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 754 days.

(21) Appl. No.: 11/502,858

(22) Filed: Aug. 11, 2006

(65) Prior Publication Data
US 2007/0128255 A1 Jun. 7, 2007

Related U.S. Application Data

(60) Provisional application No. 60/707,583, filed on Aug. 12, 2005.

(51) Int. Cl.
*G01N 33/00* (2006.01)
(52) U.S. Cl. .......... 73/866; 424/70.7; 424/62; 424/70.6; 424/401; 424/69; 424/70.1
(58) Field of Classification Search .......... None
See application file for complete search history.

(56) References Cited

U.S. PATENT DOCUMENTS

| | | | |
|---|---|---|---|
| 5,080,924 A | 1/1992 | Kamel et al. | |
| 5,260,093 A | 11/1993 | Kamel et al. | |
| 5,326,584 A | 7/1994 | Kamel et al. | |
| 5,578,079 A | 11/1996 | Kamel et al. | |
| 5,727,567 A * | 3/1998 | Carnaby et al. | 128/857 |

FOREIGN PATENT DOCUMENTS

| | | | |
|---|---|---|---|
| JP | 11-009339 | * | 1/1999 |
| JP | 11169390 A2 | | 6/1999 |

OTHER PUBLICATIONS

Kendall, 1971. The adhesion and surface energy of elastic solids. J. phys. D: Appl. Phys., vol. 4:1186-1195.*
Hamerli et al, 2003. Enhanced tissue-compatibility of polyethylenterephtalat membranes by plasma aminofunctionalisation. Surface and Coatings Tzechnology, vol. 174-175:574-578.*
Bio Skin Doll, Beaulax Co. Product Information, www.beaulax.co.ip/bio/index2_e.htm, five pages.

* cited by examiner

*Primary Examiner* — Patricia A Duffy
*Assistant Examiner* — Garen Gotfredson
(74) *Attorney, Agent, or Firm* — Melody A. Jones

(57) ABSTRACT

Article of manufacture comprising a substrate and a coating layer. The coating layer comprises at least one coating material, and is stably affixed to the substrate to form a stable, coated surface. The coated surface has a texture that mimics the topography of mammalian keratinous tissue and demonstrates at least one physical property representative of mammalian keratinous tissue, selected from the group consisting of a total surface energy of from about 15 mJ/m$^2$ to about 50 mJ/m$^2$, a dispersive component of the surface energy of from about 15 mJ/m$^2$ to about 50 mJ/m$^2$, a polar component of the total surface energy of from about 1 mJ/m$^2$ to about 14 mJ/m$^2$, a zeta-potential at a pH of about 5.0 of from about −40 mV to about 30 mV, and combinations thereof.

10 Claims, No Drawings

COATED SUBSTRATE WITH PROPERTIES OF KERATINOUS TISSUE

CROSS REFERENCE TO RELATED APPLICATION

This application claims the benefit of U.S. Provisional application Ser. No. 60/707,583 filed Aug. 12, 2005.

FIELD OF THE INVENTION

The present invention relates to an article of manufacture comprising a substrate and at least one coating layer, useful as a model of mammalian keratinous tissue.

BACKGROUND OF THE INVENTION

Many consumer products are applied to the skin or hair, and/or involve the sensory experience of touching. Consumer preferences are influenced by a multitude of factors, including product effectiveness, the feel of the product, fragrance, durability, ease of rinsing, etc. One way to determine consumer preferences is by conducting consumer marketing tests, in which a representative group of consumers, or panelists, provide feedback after using a product. Consumer marketing tests have several drawbacks, however. Because panelists must be appropriately selected and compensated for their time, such tests are expensive and time consuming. Human feedback is inherently subjective, and may raise concerns about reliability. Products must be safe for human testing, and the analyses that can be performed after application also are limited.

Some product testing can be performed using model systems. Artificial substrates are available that, to some extent, imitate human skin. For example, theatrical performers often transform their appearance by using molded body parts that can be made to look remarkably like human skin. Alternatively, keratinous tissue from animals or human cadavers may be used. Whereas these and other available models may be suitable for some types of product testing, all have significant limitations. Cadaver tissue is costly, and neither cadaver nor animal tissue can truly mimic living, human tissue. Artificial substrates are poorly suited to assess characteristics such as product adsorption, rinseability, elasticity and compressibility. Many substrates absorb water and/or decompose, and thus cannot be effectively cleaned or reused. Currently available models also fail to reflect differences in skin on various parts of the body, in different environments, and between different individuals, which may be critical in developing certain personal care products. Characteristics of skin on, for example, one's face, fingertips, palms of the hand, heels, and underarms tend to differ dramatically. The skin of babies and young children differs from the skin of adults, and skin having hair differs from non-haired skin. In summary, to date no suitable substrate is available that can reproduce complex properties of various types of keratinous tissue that are relevant to a wide range of products.

There exists a need, therefore, to provide a more suitable model of a range of types of mammalian keratinous tissue for testing consumer products, which is capable of reproducing a wide range of properties most relevant to a given product, and which can reduce the need for testing with human subjects.

SUMMARY OF THE INVENTION

The present invention meets the aforementioned need. Applicants have found that a coating layer can be stably affixed to the surface of a suitable substrate to produce a more suitable model of keratinous tissue. The coating layer can be chosen from a variety of coating materials to demonstrate known physical properties of the keratinous tissue of interest. In addition, the substrate and/or coating layer may have a texture similar to the keratinous tissue. A substance, one example of which is a consumer product, then can be topically applied to the article, which in turn can be analyzed by a wide variety of methods to gain insight into the interaction of the substance with the coated substrate. These interactions in turn can be correlated to consumer preferences, and thus aid in selective product development.

Some non-limiting physical properties of interest include surface energy (including hydrophobic and hydrophilic interactions), surface charge, and surface reactivity. For example, dry skin and human vulvar skin tend to be relatively hydrophobic, whereas wet skin tends to be relatively hydrophilic. If one is interested in formulating a product that more effectively adheres to skin in the shower, a coating layer similar in hydrophilicity to wet skin can be bonded to a substrate of the present invention, the product applied, rinsed, and the surface analyzed. Similarly, if one is interested in formulating a composition that effectively transfers from the surface of a product (for example, from a wipe or catamenial product) and effectively adheres to, for example, vulvar skin, a coating layer similar in hydrophobicity to vulvar skin can be bonded to a substrate, the product applied, and the surface analyzed. In addition, skin has a net charge associated with its surface, which may be dependent upon many factors, including for example perspiration, dryness, and even one's gender. A coating layer can be bonded to the substrate to produce a desired net positive or net negative charge, which would allow selective development of products better suited to these various circumstances.

The texture of the substrate is an important aspect of the present invention. In contrast to previously available models, the texture of the article of manufacture of the present invention can more closely mimic a wide variety of keratinous tissues. Texture may be important in determining, for example, product deposition and coverage, in particular in areas of keratinous tissue having wrinkles and deep lines. Texture also may be important in determining whether a given product is effective, for example, in dark, moist environments produced by deep lines and folds of skin.

Textured, coated substrates can be produced that combine any of the aforementioned properties, resulting in models of keratinous tissue found in a variety of environments, on a variety of body parts, and on a variety of individuals. Therefore, by choosing appropriate combinations of texture and coating materials, the surface can be controllably varied to meet a wide range of product development needs.

The coated substrates of the present invention offer several advantages over both consumer marketing tests and currently available model substrates. They are cost effective, and easy to produce, store and use. The coated substrates are robust, can be effectively cleaned with a variety of solvents without substantial deterioration, and re-used. Testing can be performed more rapidly, and can more easily be repeated, resulting in increased throughput, efficiency and reproducibility. After a substance has been applied, the coated substrate can be analyzed using standard physical and analytical methods, which results in more objective and reliable data than can be obtained from human panelists. A wide variety of analyses can be performed, including destructive analyses, which are not possible to perform on human subjects. In addition, the physical properties can be selected that are beyond the parameters typically observed in human skin, which would, for example, allow mechanistic studies to be performed.

According to the first embodiment of the present invention, an article of manufacture is provided comprising a substrate and a coating layer. The coating layer comprises at least one coating material, and is stably affixed to said substrate to form a stable, coated surface. The coated surface has a texture that mimics the topography of mammalian keratinous tissue and demonstrates at least one physical property representative of mammalian keratinous tissue, selected from the group consisting of a total surface energy of from about 15 mJ/m$^2$ to about 50 mJ/m$^2$, a dispersive component of the surface energy of from about 15 mJ/m$^2$ to about 50 mJ/m$^2$, a polar component of the total surface energy of from about 1 mJ/m$^2$ to about 14 mJ/m$^2$, a zeta-potential at a pH of about 5.0 of from about −40 mV to about 30 mV, and combinations thereof.

According to a second embodiment of the present invention, an article of manufacture is provided comprising a substrate and a coating layer. The coating layer comprises at least one coating material, and is stably affixed to the substrate to form a stable, coated surface which has a texture that mimics the topography of mammalian keratinous tissue. The coating material is selected from the group consisting of allyl amines, allyl alcohols, 1,1,1-trimethyl-1-pentene, perfluoromethylcyclohexane (PFMCH) monomer, and combinations thereof Yet another embodiment provides a method for evaluating the interaction of one or more substances with mammalian keratinous tissue, comprising the step of applying at least one substance to an article of manufacture as described in either of the preceding embodiments.

Yet another embodiment provides a process for manufacturing the article of manufacture described herein.

Yet another embodiment provides an article of commerce, comprising an article of manufacture according to the first and/or the second embodiment of the present invention, and a communication describing the use of the article of manufacture described herein to mimic mammalian keratinous tissue.

DETAILED DESCRIPTION OF THE INVENTION

Whereas the specification concludes with claims that particularly point out and distinctly claim the present invention, it is believed that the invention will be better understood from the following details.

In all embodiments of the present invention, all percentages of materials in the substrate are by weight of the total substrate, unless specifically stated otherwise. All percentages of materials in an individual coating layer are by weight of the individual coating layer, unless specifically stated otherwise. All ratios are weight ratios, unless specifically stated otherwise. The number of significant digits conveys neither limitations on the indicated amounts nor on the accuracy of the measurements. All amounts indicating quantities, percentages, proportions, etc. are understood to be modified by the word "about" unless otherwise specifically indicated. All measurements are understood to be made at about 25° C. and at ambient conditions, where "ambient conditions" means conditions under about one atmosphere of pressure and at about 50% relative humidity, unless otherwise specified.

"Topical application," as used herein, means to apply or spread a composition onto the surface of the keratinous tissue and/or onto an article of manufacture as described herein.

"Keratinous tissue," as used herein, means keratin-containing layers disposed as the outer layer of mammalian epidermal tissue, including skin, hair, nails, lips, vulvar region, buttock, and nails. The vulvar region is understood to include the region from the posterior gluteal groove and perineum to the anterior mons pubis and laterally between the intertriginous zones. The keratinous tissue may be from any part of the body of the mammal, and may vary widely in characteristics that include, but are not limited to, age, condition (for example, dryness), thickness, elasticity, pigmentation, presence of blemishes and/or imperfections, etc. "Keratinous tissue" also is understood to include the outer layer of mammalian mucosal membranes, such as the alimentary canal, including the oral cavity, esophagus, stomach, intestines, nasal cavity, lips, stomach and intestines, and the vaginal canal.

"Curable," as used herein, means substrate material that initially is in a liquid state, and that may be formed into a desired shape, for example, by pouring into a mold. Solvents are allowed to evaporate or are otherwise substantially removed. The material solidifies, and may undergo a variety of chemical reactions, including, for example, crosslinking.

"Moldable," as used herein, means substrate material that may not initially be present in a liquid state, but which may be formed into a desired shape in a solid state, for example, by appropriately applying pressure to the material. Upon application of pressure, the material will substantially maintain its shape.

"Elongation range," as used herein, means the range that an article of manufacture may be elongated, or stretched, before breaking or alternatively, before becoming irreversibly unfit for the intended use. Herein, the elongation range is expressed as a percentage, and is calculated as the length of the article of manufacture after stretching divided by the length of the article of manufacture prior to stretching, the quotient of which is multiplied by 100.

"Texture," as used herein, means a series of impressions and/or elevated areas, relative to the average height of the planar surface of the textured layer.

"Resembles" or alternatively "resembling the topography," means that one of ordinary skill in the art would recognize the depth, density and arrangements of the lines and/or grooves of the article of manufacture to be similarly patterned to, or to mimic, the keratinous tissue of interest.

"Negative mold," or "negative impression," as used herein, means a mold created by placing a suitable material on the keratinous tissue or body part of interest, and removing the material from the tissue. The resulting negative mold contains an impression of the keratinous tissue or body part. The resulting negative mold subsequently can be used to create a positive mold.

"Positive mold," as used herein, means an article made from material capable of being molded or formed so as to resemble the shape of a body part or keratinous tissue of interest. Positive molds typically are made by pouring or pressing a suitable material into a negative mold. A suitable material will retain the texture and/or shape of the keratinous tissue from which the negative mold is made.

"Substrate," as used herein, means one or more materials to which a coating layer may be stably affixed. "Coating layer," as used herein, means one or more chemical moieties, or coating materials, that are stably affixed, to the substrate. When more than one substrate material and/or coating material is present, the materials may be homogenously mixed, may form discrete areas, and/or may form discrete layers.

"Homogenously mixed," as used herein, means that the substrate and/or coating materials are combined such that the chemical and physical properties of various areas of the substrate or coating layer are substantially uniform.

"Discrete area," as used herein, means that within a given layer, the substrate and/or coating materials are separated to form areas that predominantly comprise different materials or combinations of coating materials. This results in a substrate and/or coating layer that may have varying chemical and physical properties, depending upon which area of the layer is analyzed.

"Discrete layer," as used in reference to the coating layer, means that the coating materials form at least a first coating layer and a second coating layer. The first coating layer stably affixed to the substrate such that the thickness of the coating layer is substantially uniform, and the second layer similarly is stably affixed to the first coating layer. When used in reference to the substrate, the materials form a first layer, upon which a second layer is stably affixed. Additional layers may be sequentially added. Each layer may comprise the same or different materials. When a layer comprises more than one material, the materials may be homogenously mixed, may form discrete areas, and/or may be combinations thereof.

"Stably affixed," or alternatively "bonded," as used herein, means that a compound, for example a coating layer, is stably attached such that the compound remains substantially affixed during at least one use, analysis and/or cleaning. One example of a stably affixed coating layer is one which has been applied by plasma deposition as described herein. "Substantially affixed" is understood to mean any amount of coating layer that may be incidentally removed is insufficient to measurably alter the physical properties of the artificial substrate surface that are representative of keratinous tissue. "Stably affixed" further means that the compound remains substantially affixed when rinsed and/or rubbed with solvents including, but not limited to, water, detergents, alcohols (for example, methanol, ethanol and isopropanol), hydrocarbons (for example, hexane), where "rubbing" is understood to mean at least five back-and-forth motions using a paper towel or a Kimwipe™ which is soaked in the solvent. The bonding may be covalent, or may occur by any suitable means as would be understood by one of skill in the art to result in being stably affixed as defined herein. "Stably affixed" is understood not to include, for example, laminated or other coating layers which may be removed, exhibit peeling, and/or are visibly or otherwise damaged upon exposure to solvents including, but not limited to, the aforementioned solvents. "Laminated" is understood to include layers which are attached by a discrete adhesive means, for example, a glue or other chemical adhesive.

"Stable," as used herein, means that after at least one use as described herein, the chemical and/or physical properties of the article of manufacture, including but not limited to surface energy, surface charge, texture, thickness and/or mass (for example, loss of the integrity of the texture and/or gain in mass due to absorption of water or other liquids) do not exhibit a statistically significant change. When used in reference to one or more coating layers, "stable" means that the coating layer remains substantially affixed during at least one use, non-destructive types of analysis, and/or cleaning.

"Re-used," as used herein, means that a substance may be applied to the article of manufacture and data reliably obtained at least twice.

"Physical properties representative of mammalian keratinous tissue," or grammatical equivalents thereof, as used herein, means physical and/or chemical properties of the article of manufacture that are substantially similar to mammalian keratinous tissue and that may be relevant to a particular product or substance. For example, if the keratinous tissue is found to be hydrophobic and positively charged, the coated surface of the article of manufacture also will be hydrophobic and positively charged.

"Interaction of products with mammalian keratinous tissue," includes, but is not limited to, absorption, adsorption, covalent bonding, dispersion, changes in physical properties such as color, opacity, odor, texture, feel, etc.

"Products relating to keratinous tissue," as used herein means products that are applied to the keratinous tissue, are in close contact with the keratinous tissue, and/or products that involve sensory experiences via the keratinous tissue. "Products" may refer to articles of manufacture and/or compositions that are in development, as well as those that have been sufficiently developed for manufacture and sale.

I. Article of Manufacture

A. Substrate

The article of manufacture of the present invention comprises a substrate. The substrate comprises a material to which a coating layer may be stably affixed. The substrate may be smooth or textured, rigid or pliable, and may be elastic or inelastic. The substrate material may be curable, moldable, etchable, or otherwise capable of being imparted with a desired textured surface, and may comprise polymers, glass, metals, fabrics, and combinations thereof. In one embodiment, the substrate has an elongation range of less than 400%, alternatively less than 200%, and alternatively less than 100%. The substrate may be formed by, for example, using a negative mold, into which a suitable material is poured and/or pressed; extruding; and/or imprinting, etching, engraving, or otherwise imparting a texture, including with the use of a laser and/or chemicals, to a solid surface. The substrate further may comprise at least two materials, which may be homogenously mixed, may form discrete areas and/or may form discrete layers.

Examples of suitable polymer materials are disclosed in U.S. Pat. No. 6,558,422, issued to Baker et al., and include, but are not limited to polypropylene, isotactic polypropylene, polyethylene, branched polyethylene, linear polyethylene, polyethylene oxide, polyethylacrylate, polyethyleneterephthalate, polyurethane, aliphatic polyurethane, polyester, polyorthoesters, polylactic acid, polyglycolic acid, polyethylene glycol, collagen, polygalactic acid, polydioxanone, polytrimethylene carbonate copolymers, poly-ϵ-caprolactone homopolymers and copolymers, polyanhydrides, poly-a-methylstyrene, polyamide 12, polyamide 6,6, polybutylmethacrylate, polycarbonate, fluoropolymers (including polychlorotrifluoroethylene, polytrifluoroethylene, polytetrafluoroethylene, polyvinylfluoride, polyvinylidenefluoride), polyvinylchloride, polyvinylidene chloride, polydimethylsiloxane, polyetheretherketone, polymethylmethacrylate, polyethylmethacrylate, polyhexylmethacrylate, polyisobutylene, polyisobutylmethacrylate, polymethacrylic acid, polymethylacrylate, polystyrene, poly(t-butylmethacrylate), polytetrahydrofurane, polytetramethylene oxide, polyvinylacetate, polyvinyltoluene, copolymers, isomers and derivatives of any of the foregoing, and mixtures thereof. The substrate further may be comprised of metals and metal alloys, including steel, nickel, gold, silver, and mixtures thereof. In one embodiment, the substrate material is selected from the group consisting of polyurethane, polydimethylsiloxane, linear polyethylene, isostatic polypropylene, polystyrene, polyamide, and mixtures thereof. Alternatively, the substrate material is polyurethane.

The substrate may be in any shape or form suitable for application of a product and for analysis of the substrate and/or coating layer. In one embodiment, the substrate is in the form of a sheet having two substantially planar, parallel surfaces, and a substantially uniform thickness. In one embodiment, the thickness of the substrate is from about 0.001 mm to about 5.0 cm, alternatively from about 0.01 mm to about 1.0 cm, alternatively from about 0.1 mm to about 0.5 cm, and alternatively from about 0.1 mm to about 0.25 cm. In another embodiment, the substrate is substantially cylindrical, and has an average diameter of from about 0.001 mm to about 3.0 cm, alternatively from about 0.01 mm to about 1 cm, alternatively from about 0.1 mm to about 1.0 mm, and alternatively from about 0.01 mm to about 0.2 mm. In another embodiment, the substrate is in the form of a body part, for example, an arm, leg, hand, foot, finger, toe, upper torso, lower torso, buttocks, external genitalia and/or pelvic region. Alternatively, the substrate is in the form of a child's buttocks and/or pelvic region.

The substrate may be colored, white or colorless, and may be transparent or opaque. In one embodiment, the substrate is similar in color to a desired type of mammalian skin. Alternatively, the substrate is similar in color to human skin. Alternatively, the color may be altered to resemble various degrees and types of pigmentation found in human skin.

B. Texture

The article of manufacture may comprise at least one textured surface. When the article of manufacture is cylindrical, the outermost surface may be textured. The substrate may be textured, and/or the texture may result from the coating layer. The texture comprises a plurality of impressions and/or elevated areas that may be patterned and/or may be randomly arranged. The topography of the texture may vary to resemble degrees of wrinkling of keratinous tissue. Alternatively, the depth of the impressions may vary to resemble keratinous tissue ranging from relatively smooth (for example, oral mucosal linings) to deeply lined (for example, elbows or deep facial lines), and further may resemble scaly, fissured, rough, and/or otherwise visibly-textured keratinous tissue. The texture may resemble the topography of keratinous tissue on essentially any body part. The texture may resemble the topography of healthy keratinous tissue or alternatively keratinous tissue damaged by, for example, exposure to UV-rays, chemicals, and/or illness. Alternatively, a substrate may comprise discrete areas having different textures. The texture may be visible without the use of visual aids, (i.e. on a macroscopic level), or may be clearly visible only with visual aids such as a magnifying glass or microscope set at a 10× magnification setting. In one embodiment, the texture mimics the topography of mammalian keratinous tissue. Alternatively, the texture mimics the topography of human keratinous tissue. Alternatively, the texture mimics the topography of human skin. Alternatively, the texture mimics the topography of the outermost layer of mammalian hair. Alternatively, the texture mimics the topography of the outermost layer of human hair. Alternatively, natural or artificial hair may be attached or anchored in the substrate such that one end protrudes outwardly through the coating layer. Alternatively, the texture mimics a composite of topographies of keratinous tissue from a plurality of individuals, representative of an average keratinous tissue type of a given population.

The impressions may be in the form of, for example, lines or grooves, the depth of which may vary depending upon the type and condition of keratinous tissue upon which the substrate is modeled. In one embodiment, the impressions have a depth of from about 0.01 mm to about 10 mm, alternatively from about 0.01 mm to about 0.1 mm, alternatively from about 0.1 mm to about 1 mm, and alternatively from about 0.1 mm to about 0.5 mm, as measured from the average height of the planar surface of the substrate.

C. Coating Layer

The article of manufacture of the present invention may comprise at least one coating layer that is stably affixed to the substrate. The coating layer comprises at least one coating material. The thickness of the coating layer may be substantially uniform. In one embodiment, the coating material is covalently bonded to the textured surface. In another embodiment, the coating layer forms a textured surface, which is stably affixed to a textured or non-textured substrate, which may or may not be textured. The texture may result from structures in the coating layer itself, non-limiting examples of which include particulates and fibers, or alternatively may result from impressions made in the coating layer subsequent to deposition, for example, by "stamping". The coating layer may demonstrate at least one physical property that is representative of mammalian keratinous tissue, and the choice of coating material(s) will depend upon the desired physical property. When more than one coating material is used, the compounds may be homogenously mixed, may form discrete areas, and/or may form discrete layers. In one embodiment, a first discrete coating layer is stably affixed to the substrate, and at least one additional coating layer is stably affixed to the first coating layer. The additional coating layers may be made from the same or from different coating materials than the first coating layer. The thickness of the coating layer may vary, but when the underlying substrate is textured, the coating layer may be sufficiently thin so as not to mask or significantly interfere with an underlying texture, and may faithfully mimic the underlying substrate topography. In one embodiment, the thickness of an individual coating layer is a monolayer. Alternatively, the thickness of an individual coating layer is from about 0.1 nm to about 1 mm, and alternatively from about 1 nm to 0.1 mm.

In one embodiment, the coating layer may be sufficiently cleaned to allow at least one re-use. Alternatively, the coating layer may be cleaned and re-used at least five times, alternatively at least ten times, and alternatively at least 20 times.

Examples of classes of suitable coating materials include, but are not limited to, chemical functional groups, organic compounds, hydrocarbons, chemically functionalized hydrocarbons, macrocycles, lipids, proteins, hydrophilic monomers, hydrophobic monomers, polymerizable monomers, metals, particulates, and combinations thereof. Additionally or alternatively, the coating material may comprise fibrous materials. In one embodiment, the coating materials are selected from the group consisting of chemically functionalized hydrocarbons, hydrophilic monomers, hydrophobic monomers, polymerizable monomers, and combinations thereof. Alternatively, the coating material is a metal selected from the group consisting of gold, silver, nickel, and mixtures thereof. Alternatively, the coating materials are chemically functionalized hydrocarbons.

1. Chemical Functional Groups

The coating material may comprise one or more functional groups, including, but not limited to, OH; X, where X is a halogen, for example, F, Cl, Br, I; $C_1$-$C_{10}$ alkoxy, $C_1$-$C_{10}$ alkyl halide, $C_1$-$C_{10}$ aldehyde, $C_1$-$C_{10}$ ketone, $C_1$-$C_{10}$ epoxide, $C_1$-$C_{10}$ carboxylic acid, $C_1$-$C_{10}$ ester; —S—$R_1$, where $R_1$ represents H, X, $C_1$-$C_{10}$ alkyl, $C_1$-$C_{10}$ alkene, $C_1$-$C_{10}$ diene, $C_1$-$C_{10}$ alkyne, $C_1$-$C_{10}$ alkoxy, $C_1$-$C_{10}$ alkyl halide, $C_1$-$C_{10}$ aldehyde, $C_1$-$C_{10}$ ketone, $C_1$-$C_{10}$ epoxide, $C_1$-$C_{10}$ carboxylic acid, or a $C_1$-$C_{10}$ ester; $SO_3$; $SO_4$; $NH_2$ (amine); $NH_3^+$; $NO_2$; NOX; SiOx, where x has a value of from 1 to 5; Si—$R_1R_2R_3$, where $R_1$, $R_2$, and $R_3$ each independently represent H, OH, X, $C_1$-$C_{10}$ alkyl, $C_1$-$C_{10}$ alkene, $C_1$-$C_{10}$ diene, $C_1$-$C_{10}$ alkyne, $C_1$-$C_{10}$ alkoxy, $C_1$-$C_{10}$ alkyl halide, $C_1$-$C_{10}$ aldehyde, $C_1$-$C_{10}$ ketone, $C_1$-$C_{10}$ epoxide, $C_1$-$C_{10}$ carboxylic acid, or a $C_1$-$C_{10}$ ester; allyl compounds, including but not limited to allyl isothiocyanate, allyl cyanide, allyl benzene, allyl acetate, allyl mercaptan, allyl glycidyl ether, allyl ether, allyl chloroformate, allyl methyl sulfide, allyl phenyl sulfone, allylphosphonic dichloride, allyltrimethylsilane, and allyltriethoxysilane; salts of any of the above; and mixtures thereof.

2. Organic Compounds

The coating material of the present invention may comprise an organic compound, one non-limiting example of which is an organic compound having the following general structure:

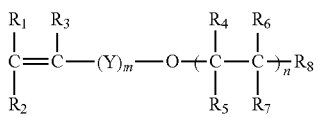

wherein $R_1$, $R_2$, $R_3$, $R_4$, $R_5$, $R_6$ and $R_7$ each independently represent: H, OH, X, $C_1$-$C_4$ alkyl, $C_1$-$C_4$ alkene, $C_1$-$C_4$ diene, $C_1$-$C_4$ alkyne, $C_1$-$C_4$ alkoxy, and/or $C_1$-$C_4$ alkyl halide; and $R_8$ represents H, a halogen, $C_1$-$C_4$ alkyl, $C_1$-$C_4$ alkene, $C_1$-$C_4$ diene, $C_1$-$C_4$ alkyne, $C_1$-$C_4$ alkyl halide, $C_1$-$C_4$ aldehyde, $C_1$-$C_4$ ketone, $C_1$-$C_4$ epoxide, $C_1$-$C_4$ carboxylic acid, $C_1$-$C_4$ ester, —CH=CH—$R_9$, where $R_9$ is H, X, $C_1$-$C_4$ alkyl, $C_1$-$C_4$ alkyl halide, $C_1$-$C_4$ aldehyde, $C_1$-$C_4$ ketone, $C_1$-$C_4$ alkoxyl, $C_1$-$C_4$ epoxide, $C_1$-$C_4$ carboxylic acid, or $C_1$-$C_4$ ester. Alternatively, $R_8$ may represent —$OR_{10}$, where $R_{10}$ is H, X, $C_1$-$C_4$ alkyl, $C_1$-$C_4$ alkene, $C_1$-$C_4$ diene, $C_1$-$C_4$ alkyne, $C_1$-$C_4$ alkyl halide, $C_{1-4}$ aldehyde, $C_1$-$C_4$ ketone, $C_1$-$C_4$ epoxide, $C_1$-$C_4$ carboxylic acid, or $C_1$-$C_4$ ester.

Examples of suitable organic coating materials include $CH_2$=CH—$(OCH_2CH_2)_n$—OH; $CH_2$=CH—$(OCH_2CH_2)_n$—$OCH_3$; $CH_2$=CH—$(OCH_2CH_2)_n$—OCH=$CH_2$; di(ethylene glycol) divinyl ether, or $(H_2C$=$CHOCH_2CH_2)_2O$; di(ethylene glycol) vinyl ether, or $H_2C$=$CH(OCH_2CH_2)_2$OH; di(ethylene glycol) methyl vinyl ether, or $H_2C$=CH $(OCH_2CH_2)_2OCH_3$; di(ethylene glycol) diacrylate, or $(H_2C$=$CHCO_2CH_2CH_2)_2O$; di(ethylene glycol) ethyl ether acrylate, or $H_2C$=$CHC(O)(OCH_2CH_2)_2OC_2H_5$; trimethylolpropane diallyl ether, or $C_2H_5C(CH_2OCH_2CH$=$CH_2)_2$ $CH_2OH$; tetra(ethylene glycol) propyl ether methacrylate, or $H_2C$=$C(CH_3)CO_2(OCH_2CH_2)_4CH_2CH_2CH_3$; hexa(ethylene glycol) methyl ether methacrylate, or $H_2C$=$C(CH_3)CO_2$ $(OCH_2CH_2)_6CH_3$; aliphatic polyurethane, non-polyester-based polyurethanes, and combinations thereof. Alternatively, the organic coating material is selected from the group consisting of di(ethylene glycol) divinyl ether, di(ethylene glycol) methyl vinyl ether, di(ethylene glycol) ethyl ether acrylate, trimethylisopropane diallyl ether, aliphatic polyurethane, derivatives of any of the above, and mixtures thereof.

2. Hydrocarbons

The coating material of the present invention may comprise a hydrocarbon. The hydrocarbon may be straight-chained or branched, linear or cyclic, and may comprise alkyl, alkenyl and alkynyl moieties. In one embodiment, the hydrocarbon comprises from about 1 to about 50 carbon atoms, alternatively from about 1 to about 30 carbon atoms, and alternatively from about 1 to about 20 carbon atoms. Alternatively, the hydrocarbon comprises from about 4 to about 12 carbon atoms. Alternatively, the hydrocarbon is selected from the group comprising pentenes, hexenes and combinations thereof. Alternatively, the hydrocarbon is 1,1,1-tri-methyl-1-pentene.

3. Chemically Functionalized Hydrocarbons

The coating material of the present invention may comprise a chemically functionalized hydrocarbon, in which a hydrocarbon coating material may be modified to replace from one to three hydrogen atoms with $R_1$, $R_2$, and $R_3$ respectively, where $R_1$, $R_2$, and $R_3$ each independently represent OH, X, $C_1$-$C_{10}$ alkoxy, and/or $C_1$-$C_{10}$ alkyl halide; $C_1$-$C_{10}$ aldehyde, $C_1$-$C_{10}$ ketone, $C_1$-$C_{10}$ epoxide, $C_1$-$C_{10}$ carboxylic acid, $C_1$-$C_{10}$ ester, $C_1$-$C_{10}$ thiol, $NH_2$ (amine), $NH_3^+$, $NO_2$, NOX, $CF_3$, $CF_2$; $C_xH_yF_z$, where x represents an integer of from 1 to 10, and y and z represent appropriate stoichiometric values; $CF_xX_y$, where x represents 1 or 2, and y represents an integer having an appropriate stoichiometric value of 1 or 2; S—$R_1$, where $R_1$ represents H, X, $C_1$-$C_{10}$ alkyl, $C_1$-$C_{10}$ alkene, $C_1$-$C_{10}$ diene, $C_1$-$C_{10}$ alkyne, $C_1$-$C_{10}$ alkoxy, $C_1$-$C_{10}$ alkyl halide, $C_1$-$C_{10}$ aldehyde, $C_1$-$C_{10}$ ketone, $C_1$-$C_{10}$ epoxide, $C_1$-CIO carboxylic acid, or a $C_1$-$C_{10}$ ester; allyl compounds, including but not limited to allyl isothiocyanate, allyl amines, allyl cyanide, allyl benzene, allyl acetate, allyl mercaptan, allyl glycidyl ether, allyl ether, allyl chloroformate, allyl methyl sulfide, allyl phenyl sulfone, allylphosphonic dichloride, allyltrimethylsilane, and allyltriethoxysilane; salts and derivatives of any of the above, and mixtures thereof.

Alternatively, one or more hydrogen atoms may be replaced with $SiO_x$, where x has a value of from 1 to 5, and/or Si—$R_1R_2R_3$, where $R_1$, $R_2$, and $R_3$ each independently represent H, OH, X, $C_1$-$C_{10}$ alkyl, $C_1$-$C_{10}$ alkene, $C_1$-$C_{10}$ diene, $C_1$-$C_{10}$ alkyne, $C_1$-$C_{10}$ alkoxy, $C_1$-$C_{10}$ alkyl halide; $C_1$-$C_{10}$ aldehyde, $C_1$-$C_{10}$ ketone, $C_1$-$C_{10}$ epoxide, $C_1$-$C_{10}$ carboxylic acid, $C_1$-$C_{10}$ ester, $C_1$-$C_{10}$ thiol, $NH_2$, $NH_3^+$, $NO_2$, NOX, $CF_3$, $CF_2$; $C_xH_yF_z$, where x represents an integer of from 1 to 10, and y and z represent appropriate stoichiometric values; $CF_xX_y$, where x represents 1 or 2, and y represents an integer having an appropriate stoichiometric value of 1 or 2; SH, COX, COOH, salts and derivatives of any of the above, and mixtures thereof.

In one embodiment, the hydrocarbon is modified with a chemical moiety selected from the group consisting of amines, alcohols, and combinations thereof. Alternatively, the chemically functionalized hydrocarbon is an allyl amine, allyl alcohol, and mixtures thereof. Alternatively, the hydrocarbon is modified with at least two distinct functional, or $R_1$, $R_2$, and $R_3$, groups.

4. Macrocycles

The coating material of the present invention may comprise a macrocycle. As used herein, "macrocycle" means compound comprising at least one cyclic structure comprised of carbon atoms, hydrogen atoms, at least one hetero-atom, non-limiting examples of which include oxygen, nitrogen and sulfur. In one embodiment, the macrocycle of the present invention comprises a cyclic ether, for example, ethylene oxide, dioxane, and/or a crown ether. Alternatively, the macrocycle is a crown ether. Examples of suitable crown ethers include, but are not limited to, 12-crown-4, 15-crown-5, 18-crown-6, dicyclyhexano-18-crown-6, 4'-aminobenzyl-15-crown-5, 2-(aminomethyl)-12-crown-4, 2-(aminomethyl)-15-crown-5, 2-(aminomethyl)-18-crown-6, 1-aza-12-crown-4, 1aza-15-crown-5, 1-aza-18-crown-6, benzo-12-crown-4, benzo-15-crown-5, benzo-18-crown-6, bis[(benzo-15-crown-5)-15-ylmethyl]pimelate, 4'bromobenzo-18-crown-6, dibenzo-18-crown-6, dibenzo-24-crown-8, dibenzo-30-crown-10, dicyclohexano-24-crown-8, 4'-formylbenzo-15-crown-5, 2-(hydroxymethyl)-12-crown-4, 2-(hydroxymethyl)-15-crown-5, 2-(hydroxymethyl)-18-crown 6, 4'nitrobenzo-15-crown-5, poly[(dibenzo-18-crown-6)-co-formaldehyde], derivatives of any of the above, and mixtures thereof.

5. Hydrophilic Monomers

The coating material of the present invention may comprise a hydrophilic monomer. Suitable organic hydrophilic monomers include water soluble conventional vinyl monomers such as acrylates and methacrylates of the general structure $H_2C$=$CR_1$—C—$COOR_2$, where $R_1$ is hydrogen or methyl, and $R_2$ is hydrogen or is an aliphatic hydrocarbon group of up to about 10 carbon atoms substituted by one or more water solubilizing moieties, including carboxyl, hydroxyl, amino, lower alkylamino, lower dialkylamino, polyethylene oxides having from 2 to about 100 repeating units, or wherein $R_2$ is an aliphatic hydrocarbon group substituted by one or more sulfate, phosphate, sulfonate, phosphonate, carboxamido, sulfonamido or phosphonamido moeities, acrylamides and methyacrylamides of the formula $H_2C=CR_1—CONHR_2$ where $R_1$ and $R_2$ are as defined above; acrylamides and methyacrylamides of the formula $H_2C=CR_1—CON(R_3)_2$ where $R_3$ is lower alkyl of 1 to 3 carbon atoms and $R_1$ is as defined above; maleates and fumarates of the formula $R_2OOCCH=CH—COOR_2$ wherein $R_2$ is as defined above; vinyl ethers of the formula $H_2—CH=CH—O—R_2$, where $R_2$ is as defined above; aliphatic vinyl compounds of the formula $R_1—CH=CHR_2$ where $R_1$ is as defined above and $R_2$ is as defined above with the proviso that $R_2$ is other than hydrogen; vinyl substituted heterocycles, such as vinyl pyridines, piperidines and imidazoles and N-vinyl lactams, such as N-vinyl-2-pyrrolidone, derivatives of any of the above, and mixtures thereof.

Alternatively, the coating material of the present invention may comprise 2-hydroxyethyl-, 2- and 3-hydroxypropyl-, 2,3-dihydroxypropyl-, polyethoxyethyl-, and polyethoxypropyl acrylates, methacrylates, acrylamides and methacrylamides; acrylamide, methacrylamide, N-methylacrylamide, N-methylmethacrylamide, N,N-dimethylacrylamide, N,N-dimethylmethacrylamide; N,N-dimethyl- and N,N-diethylaminoethyl acrylate and methacrylate and the corresponding acrylamides and methacrylamides; 2- and 4-vinylpyridine; 4- and 2-methyl-5-vinylpyridine; N-methyl-4-vinylpiperidine; 2-methyl-1-vinylimidazole; N,N-dimethylamine; dimethylaminoethyl vinyl ether, N-vinylpyrrolidone; acrylic and methacrylic acid; itaconic, crotonic, fumaric and maleic acids and the lower hydroxyalkyl mono and diesters thereof, such as the 2-hydroxyethyl fumarate and maleate, sodium acrylate and methacrylate; maleic anhydride; 2-methacryloyloxyethylsulfonic acid and allylsulfonic acid, derivatives of any of the above, and mixtures thereof. Alternatively, the coating material of the present invention comprises 2-hydroxyethyl-methacrylate; N,N-dimethylacrylamide; acrylic acid, methacrylic acid, and mixtures thereof, and alternatively 2-hydroxyethyl methacrylate.

6. Hydrophobic Monomers

The coating material of the present invention may comprise a hydrophobic monomer. One example of a suitable class of hydrophobic monomers is fluoromonomers, and include but not limited to, fluoroacrylate monomers, fluoroolefin monomers, fluorostyrene monomers, fluoroalkylene oxide monomers (for example, perfluoropropylene oxide, perfluorocyclohexene oxide), fluorinated vinyl alkyl ether monomers, and the copolymers thereof with suitable comonomers, wherein the comonomers may be fluorinated or non-fluorinated; derivatives of any of the above and mixtures thereof. In one embodiment, the fluoromonomers are polymerized by a free radical polymerization process. In one embodiment, the coating material comprises perfluoromethylcyclohexane (PFMCH) monomer.

Alternatively, the coating material may comprise fluorostyrenes and fluorinated vinyl alkyl ether monomers, which include, but are not limited to, α-fluorostyrene; β-fluorostyrene; α,β-difluorostyrene; β,β-difluorostyrene; α,β,β-trifluorostyrene; α-trifluoromethylstyrene; 2,4,6-Tris (trifluoromethyl)styrene; 2,3,4,5,6-pentafluorostyrene; 2,3,4,5,6-pentafluoro-a-methylstyrene; 2,3,4,5,6-pentafluoro-β-methylstyrene; derivatives of any of the above and mixtures thereof.

Alternatively, the coating material may comprise tetrafluoroethylenes, which include, but are not limited to, tetrafluoroethylene-hexafluoropropylene copolymers, tetrafluoroethylene-perfluorovinyl ether copolymers (for example, copolymers of tetrafluoroethylene with perfluoropropyl vinyl ether), tetrafluoroethylene-ethylene copolymers, perfluorinated ionomers (for example, perfluorosulfonate ionomers; perfluorocarboxylate ionomers; derivatives of any of the above and mixtures thereof.

Alternatively, the coating material may comprise fluorocarbon elastomers, which include but are not limited to, poly (vinylidene fluoride-co-hexafluoropropylene);

poly(vinylidene fluoride-co-hexafluoropropylene-co-tetrafluoroethylene); poly[vinylidene fluoride-co-tetrafluoroethylene-co-perfluoro(methyl vinyl ether)]; poly[tetrafluoroethylene-co-perfluoro(methyl vinyl ether)]; poly (tetrafluoroethylene-co-propylene; poly(vinylidene fluoride-co-chlorotrifluoroethylene), derivatives of any of the above and mixtures thereof.

Alternatively, the coating material may comprise fluoroacrylate monomers. "Fluoroacrylate monomer," as used herein, means esters of acrylic acid, wherein the esterifying group is a fluorinated group such as perfluoroalkyl. A specific group of 10 fluoroacrylate monomers useful in the present invention are compounds represented by formula $H_2C=CR_1—COO(CH_2)_n—_2$, where n is 1 or 2; $R_1$ is hydrogen or methyl; and $R_2$ is a perfluorinated aliphatic or perfluorinated aromatic group, such as a perfluorinated linear or branched, saturated or unsaturated $C_1$ to $C_{10}$ alkyl, phenyl, or naphthyl. Alternatively, $R_2$ is a $C_1$ to $C_8$ perfluoroalkyl, or alternatively $—CH_2—NR_3—SO_2—R_4$, wherein $R_3$ is $C_1$-$C_2$ alkyl and $R_4$ is $C_1$ to $C_8$ perfluoroalkyl. "Perfluorinated," as used herein, means that all or essentially all hydrogen atoms are replaced with fluorine.

Monomers illustrative of the above formula, and their abbreviations, include 2-(N-ethylperfluorooctanesulfonamido) ethyl acrylate ("EtFOSEA"); 2-(N-ethylperfluoroctanesulfonamido) ethyl methacrylate ("EtFOSEMA"); 2-(N-methylperfluorooctanesulfonamido) ethyl acrylate ("MeFOSEA"); 2-(N-methylperfluoroctanesulfonamido) ethyl methacrylate ("MeFOSEMA"); 1,1-Dihydroperfluorooctyl acrylate ("FOA"); and 1,1-Dihydroperfluorooctyl methacrylate ("FOMA").

7. Polymerizable Monomers

The coating material of the present invention may comprise a polymerizable monomer. Examples of suitable polymerizable monomers include acrylic and methacrylic acid of the general formula $H_2C=C(R_2)—C(O)OH$, acrylates and methacrylates of the general formula $H_2 C=C(R2)—C(O)OR3$, acrylamides and methacrylamides of the general formula $(R2)(R2)C=C(R2)—C(O)NHR3$, maleic and fumaric acid of the general formula $HO(O)C—C(R2)=C(R2)—C(O)OH$, maleates and fumarates of the general formula $R_3O(O)C—C(R2)=C(R2)C(O)OR3$, vinyl ethers of the general formula $(R2)(R2)C=C(R2)—O—R3$, N-vinyl-2-pyrolidone of the formula $(R2)(R2)C=C(R2)—N—CH_2—CH_2—CH_2—C(O)$, vinyl acetate of the general formula $(R2)(R2)C=C(R2)—OC(O)CH_3$, aliphatic vinyl compounds of the general formula $R_2CH=CHR_3$, derivatives of any of the above, and mixtures thereof; where each $R_2$ is independently hydrogen or $C_1$-$C_{10}$ alkyl, and each $R_3$ is independently an aliphatic hydrocarbon having from 1 to about 10 carbon atoms, wherein the carbon atoms are may be unsubstituted, or substituted by one or more moieties such as —COOH, —NH2, a (poly)ethylene oxide group optionally substituted by one or more moieties such as sulfate, phosphate, or sulfonate groups; salts and derivatives of any of the above; and mixtures thereof. Alternatively, the polymerizable liquid monomer is selected from the group consisting of fluoromono and polyacrylate, fluoroolefin, fluorostyrene, fluoroalkylene oxide, fluorinated vinyl alkyl ether monomers, or the copolymers thereof with suitable comonomers, wherein the comonomers are fluorinated or unfluorinated.

Alternatively, the coating layer of the present invention may include monomeric materials suitable for use in the process of flash evaporation and cryo-condenstation, described in U.S. Pat. Nos. 4,842,893 and 4,954,371, both issued to Yializis et al. Suitable compounds include polyfunctional acrylates having a molecular weight of from about 150 to 1000 grams/mole, an average of two or more double bonds, and a vapor pressure of from about $1\times10^{-6}$ Torr to about 0.1 Torr, and alternatively a vapor pressure of approximately 0.01 Torr, where the vapor pressure is measured at standard temperature and pressure. One example of a suitable polyfunctional acrylate has the general formula:

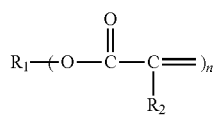

wherein $R_1$ is an aliphatic, alicyclic or mixed aliphatic-alicyclic radical derived from a compound of the formula $R_1(OH)_m$, where n has a value of between 2 and 4 and m has a value of at least 2; and $R_2$ is hydrogen, methyl, ethyl, propyl, butyl or pentyl.

7. Particulates

The coating material of the present invention may comprise one or more particulates. The particulates may be a variety of shapes, for example, be platelet-shaped, spherical, elongated or needle-shaped, or irregularly shaped, and may be surface coated or uncoated, porous or non-porous, charged or uncharged, and can be added to the current compositions as a powder or as a pre-dispersion. These particulate materials can be derived from natural and/or synthetic sources. The particulate materials may be incorporated into the coating layer prior to bonding and/or applied as an additional coating layer after bonding of a first coating layer. The particulate material may contribute to or result in formation of a texture that resembles mammalian keratinous tissue. The particulate material further may contribute to or result in surface heterogeneity of properties representative of keratinous tissue. In one non-limiting example, a coating layer may be formulated to demonstrate properties of the intercellular material in the stratum corneum and include particulates which demonstrate properties of the stratum corneum cells.

Nonlimiting examples of particulate materials useful in the present invention can be found in The Cosmetic, Toiletry, and Fragrance Association's *The International Cosmetic Ingredient Dictionary and Handbook*, $10^{th}$ Ed., Gottschalck, T. E. and McEwen, Jr., Eds. (2004), p. 2728. Other examples of particulate materials useful in the present invention include colored and uncolored pigments, interference pigments, inorganic powders and organic powders other than those described above, composite powders, optical brightener particles, and mixtures thereof. The average size of such particulates in general may be smaller than the aforementioned particulate materials, ranging for example from about 0.1 microns to about 100 microns. The pigments and/or powders of the current invention may be surface treated to provide added stability of color and/or for ease of formulation. Nonlimiting examples of suitable coating materials include silicones, lecithin, amino acids, metal soaps, polyethylene, collagen, and combinations thereof.

D. Bonding of Coating Layer

The coating layer may be stably affixed to the substrate and/or other coating layer by any process which results in formation of a stable coating layer. The process may result in covalent bonds being formed between the coating layer and the substrate, or alternatively between two coating layers, or the process may result in other types of stable bonds. The bonding process may require the steps of surface activation; deposition of the coating material; and bonding the coating material to the activated substrate. Alternatively, curing may be required to further stabilize the coating material. Alternatively, the coating layer may be bonded by means of self-assembly, one non-limiting example of which is bonding of a sulfur-containing moiety to a metallic surface to produce what is known in the art as a self-assembled monolayer.

Surface activation may be required to make the surface chemically reactive and thus prepare the substrate for deposition of a coating layer. Surface activation may occur by a variety of means, non-limiting examples of which include plasma activation, electron beam activation, corona activation, glow discharge activation, optical activation, and combinations thereof. Surface activation may occur either at or below atmospheric pressure. In one embodiment, surface activation occurs by means of plasma activation. Plasma activation may occur with radio-frequency generated plasma or with microwave-frequency generated plasma. An example of a suitable atmospheric-pressure plasma generating apparatus and bonding process is described in U.S. Pat. No. 6,821,379, issued to Datta et al. An example of a suitable microwave-frequency generated plasma apparatus and bonding process is described in U.S. Pat. No. 6,841,201, issued to Shanov et al.

Deposition of the coating material also may occur through a variety of means, non-limiting examples of which include exposure of the activated surface to the coating material in the gas phase and/or exposure to the coating material in the liquid phase, for example by spin coating, spray coating, or dip coating, provided that the deposition results in a stably bonded coating layer. Processes that result, for example, in a laminated coating that can be manually peeled or removed by rubbing and/or with commonly available solvents are not considered to be stably affixed, as defined herein. In one embodiment, the coating material is deposited in the gas phase, for example by plasma deposition. Alternatively, the coating material is deposited by means of flash evaporation and cryo-condenstation.

Bonding and/or curing may be required subsequent to deposition to sufficiently adhere the coating layer to the substrate and to otherwise stabilize the coating layer. Methods of bonding include, but are not limited to, polymerization, crosslinking, including e-beam crosslinking, photo-crosslinking, and/or thermal cross-linking, and combinations thereof. The methods of inducing chemical bonding may include application of energy in the form of heat, light, radio-frequency, microwave, and/or ultrasound energy. The energy may be applied in a pulsed and/or continuous manner.

Alternatively, activation, deposition and/or bonding may occur by means of a single process. For example, both surface activation and deposition (or "grafting") may occur as a result of the plasma deposition process described in U.S. Pat. No. 6,821,379, issued to Datta et al., and U.S. Pat. No. 6,841,201, issued to Shanov et al.

E. Physical Properties Representative of Mammalian Keratinous Tissue

The article of manufacture of the present invention demonstrates one or more physical properties that are representative of mammalian skin. The property or properties of interest will vary according to factors that include, but are not limited to, the type of keratinous tissue, the environment of the keratinous tissue, the individual consumer, the substance that is being applied to the keratinous tissue and/or the product with which the keratinous tissue comes into contact. Examples of representative properties include, but are not limited to, surface energy (for example, hydrophobicity and hydrophilicity), surface charge, surface reactivity, texture, and combinations thereof. The properties can be controllably varied by, for example, the choice of substrate and/or coating layer, and by varying parameters that control deposition of the coating layer.

The coating layer may have an average surface charge that is representative of mammalian keratinous tissue. Herein, the surface charge of the coating layer is understood to mean the average surface charge of a representative area of coating layer, although localized variations may occur due to such factors as variation of deposition of coating materials (e.g. proteins and lipids) and texture. The surface charge of the coating layer may be positive, negative, or neutral, and is largely determined by the presence of ionic species, including acidic and basic species. The surface charge determines, for example, the polarity of the keratinous tissue, which in turn may affect deposition and adhesion of various substances on the surface. The net surface charge may be measured by determination of the isoelectric point and/or the zeta-potential of the surface. A variety of means of determining the zeta-potential may be employed and would be known to one of skill in the art. For the purposes of the present invention, determine the zeta-potential of the coated substrates by streaming potential measurements conducted on an Electro Kinetic analyzer (model no. BI-EKA, Anton Parr GmbH, Brookhaven Instruments Corporation, New York, N,Y.) with a clamp cell configuration, using as an electrolyte solution $1.0 \times 10^{-3}$ M KCl in deionized water, titrated starting from a pH of about 2.5 to a pH of about 8.0 using a 1N solution of NaOH. The zeta potential values generated as a function of pH are relative to standard PMMA (polymethyl methacrylate). Each zeta-potential profile (for each type of coated substrate and other model) can thus be compared in relative terms.

In one embodiment, the zeta-potential of the coating layer at a pH of about 5.0 is from about −40 mV to about +30 mV, where "mV" means $1 \times 10^{-3}$ Volts. In one embodiment, the zeta-potential of the coating layer at a pH of about 5.0 is from about −15 mV to about +15 mV, where "about 5.0" is understood to mean 5.0±0.3 pH units.

The coating layer may have an average surface energy that is representative of mammalian keratinous tissue. Herein, the surface energy of the coating layer is understood to mean the average surface energy of a representative area of coating layer, although localized variations may occur due to such factors as variation of deposition of coating materials (e.g. proteins and lipids) and texture. The surface energy of the coating layer correlates to hydrophobicity and hydrophilicity, and may be representative of, for example, the moisture content of keratinous tissue. The surface energy of the coating layer are derived from contact angle measurements, which can be converted to surface energy by various accepted models that would be known to one of skill in the art. One such model, used in the present invention, is the Fowkes equation, as described in Fowkes, F. M.: *Industrial and Engineering Chemistry*, vol. 56, number 12, p. 40 (1964):

$$\gamma_{lv}(1+\cos\theta) = 2(\gamma_{lv}^{d}\gamma_{sv}^{d})^{1/2} + 2(\gamma_{lv}^{p}\gamma_{sv}^{p})^{1/2}$$

where $\theta$ refers to the contact angle; $\gamma_{lv}$ refers to the surface tension of liquid; $\gamma_{lv}^{d}$ refers to is the dispersive component of the surface tension of liquid; $\gamma_{sv}^{d}$ refers to the dispersive component of the surface tension of solid; $\gamma_{lv}^{p}$ refers to the polar component of the surface tension of liquid and $\gamma_{sv}^{p}$—is the polar component of the surface tension of solid. The contact angles of the coated substrates of the present invention were measured using diiodomethane (99%, Aldrich), ethylene glycol (99%+, Aldrich) and water (HPLC grade, Aldrich).

The total surface energy of the coating layer is the sum of the dispersive surface energy component and the polar surface energy component, which is thought to affect properties such as adhesion of substances to the coating layer. In one embodiment, the coating layer has a total surface energy of from about 15 mJ/m² to about 50 mJ/m², alternatively from about 20 mJ/m² to about 40 mJ/m² and alternatively from about 28 mJ/m² to about 35 mJ/m², where "mJ" means $1 \times 10^{-3}$ Joules and "m²" means square meters. In one embodiment, the coating layer has a polar surface energy component of from about 0 mJ/m² to about 15 mJ/m². Alternatively, the polar surface energy component is from about 0 mJ/m² to about 5 mJ/m², alternatively from about 7 mJ/m² to about 13 mJ/m², and alternatively from about 13 mJ/m² to about 20 mJ/m².

The coating layer may have a surface reactivity that is representative of mammalian keratinous tissue. Surface reactivity is understood to include an increased tendency to react with, or alternatively to bond to, a given compound. Surface reactivity may be determined by a variety of methods, including, for example, measurement of binding coefficients. In contrast to surface charge, which relates to the presence of ionic species, surface reactivity is understood to encompass other types of chemical interactions, for example, covalent interactions. One non-limiting example of surface reactivity would be that exhibited by a thiol-containing coating material toward nucleophilic chemical moieties, for example gold or silver, in products and/or substances.

II. Method of Use

The present invention further describes a method of evaluating the interaction of one or more substances with mammalian keratinous tissue. The method comprises the step of applying a substance to an article of manufacture as described herein. The substance may be applied directly, or may be applied by bringing a second article of manufacture, non-limiting examples of which include a wipe or an absorbent article, into contact with the coated substrate of the present invention. The method further may comprise the step of performing chemical and/or instrumental analysis of the coated substrate, the second article of manufacture, and/or the substance of interest. In one embodiment, the binding coefficient of the substance to the coating layer may be determined. Alternatively, the substance may be removed from the article of manufacture, for example by rinsing, wiping, or other suitable means, prior to, during and/or after analysis. The method may be performed under static conditions or with dynamic movement, at room temperature, or at body temperature. Alternatively, the substrate may be pre-conditioned to specified environmental conditions, for example, temperature, humidity, UV-radiation, light, exposure to additional substances, etc. In one embodiment, the steps of applying a substance, performing analysis, and optionally removing the substance, may be repeated at least once, alternatively at least five times, alternatively at least ten times, and alternatively at least twenty times. In one embodiment, the transfer of a substance from a product (non-limiting examples of which include absorbent products such as a wipe, diaper, catamenial pad, etc) to the coated substrate may be determined. Alternatively, the transfer of a substance from the coated substrate to a product may be determined.

The substance of the present method may be a product, for example a consumer product, a natural substance, and/or an imitation of a natural substance. Examples of products include, but are not limited to, skin care products, including moisturizers, cleansers and combinations thereof; cosmetics; hair care products, including shampoos, conditioners, styling agents, bleaches, colorants, and combinations thereof; deodorants; antiperspirants; perfumes; deodorizers; fabric care products, including softeners, detergents, cleansers, whiteners and deodorizers; adhesive products, including dermal and transdermal delivery systems, bandages and temperature change elements (e.g. devices for cooling and/or applying heat); active ingredients, whether applied directly or delivered by a device such as an adhesive product or delivery enhancement device; absorbent products, such as facial tissue, toilet tissue, paper towels, catamenial pads, and tampons; baby care products, including diapers, wipes, cleansers, conditioners; adult incontinence products; and combinations of any of the foregoing. Examples of natural substances include, but are not limited to, bodily fluids such as blood, menstrual fluid, urine; bodily waste, such as perspiration, feces and mucosal secretions; plant products, for example, grass stains, pollen and other allergens; and combinations of these and/or any of the aforementioned products. Alternatively, the substance may be an imitation of any of the aforementioned natural substances, which has properties similar to those of interest in the natural product.

A wide variety of interactions of the substance with the article of manufacture may be evaluated, including but not limited to: absorption; adsorption; ease of rinsing; adherence and/or distribution of a product, bodily fluid and/or bodily waste; adherence of a substance upon rinsing; glide; greasiness; stickiness; smoothness; coverage; stability; skin feel; distribution; changes in physical properties such as color, opacity, odor and texture; and combinations of any of the foregoing.

A wide variety of amounts of substance may be applied to the article of manufacture, and will depend upon such factors as the substance and the intended use thereof. In one embodiment, the amount of substance applied is the amount of a particular substance that a consumer is instructed to topically apply, or alternatively, the amount of a substance that a consumer would reasonably be expected to topically apply. In one embodiment, the amount applied to the article of manufacture is from about 0.1 mg/cm$^2$ to about 1.0 g/cm$^2$. Alternatively, the amount of substance applied represents an amount that would be expected to occur as a result of normal bodily functions, or of normal physical activities, for example, working or playing outdoors.

The present invention further provides for a method of product testing comprising the step of placing an article of manufacture as described herein in a testing apparatus, and using the article of manufacture to facilitate analysis of a product. In contrast to the method of evaluating the interaction of a substance with mammalian keratinous tissue, in which the article of manufacture itself is analyzed, here the coated substrate itself is not analyzed, but rather facilitates the use and/or analysis of a product or substance. In one embodiment of this method, the article of manufacture comprises a textured substrate, as described herein, and demonstrates at least one physical property representative of mammalian keratinous tissue. Alternatively, the article of manufacture comprises at least one coating layer, as described herein, wherein said coating layer is stably affixed to a textured surface of the substrate.

Article of Commerce

The present invention provides for an article of commerce, or alternatively for a kit, comprising an article of manufacture as described herein, and a communication describing the use of said article of manufacture to mimic mammalian skin and/or to evaluate the interaction of at least one substance with said article of manufacture. The communication may be printed material attached directly or indirectly to packaging that contains the article of manufacture. Alternatively, the communication may be placed directly or indirectly near a container. Alternatively, the communication may be an electronic or a broadcast message that is associated with the article of manufacture. Alternatively, the communication may describe at least one possible use, capability, distinguishing feature and/or limitation of the article of manufacture.

In one non-limiting example of an article of commerce of the present invention, an article of manufacture comprising a suitable substrate material is packaged together with a sheet of printed instructions. The substrate material has a surface texture resembling mammalian keratinous tissue, for example, skin or hair. The instructions communicate, among other things, the intended use of the substrate, how to properly apply a substance to the substrate, and how to clean the substrate prior to re-use.

In another non-limiting example of an article of commerce of the present invention, a package contains an article of manufacture comprising a suitable substrate material onto which a coating layer has been stably affixed. A printed advertisement, for example, in a trade journal, refers to the article of manufacture contained in the package and communicates that the substrate and coating material are suitable for testing consumer products.

IV. EXAMPLES

Example 1

The following example illustrates one process of creating a mold and imparting to the substrate a texture that has been modeled directly from the skin.

Make a first negative imprint of keratinous tissue by applying a material[1] capable of forming a cast, or mold, onto a body part, for example, human skin and/or hair. Remove the cast and allow to dry for 3-7 min. Make a positive mold that resembles the body part in both form and texture by placing for example silicone or other suitable material[2] in the negative mold. Impress the positive mold into polyurethane or other suitable material to create a second negative mold, and allow the second negative mold to cure overnight. Optionally, press the positive molds into a unitary mold of polyurethane or other suitable material to create multiple negative molds. Optionally, coat the second negative mold with a 1:1 mixture of Skin-Flex SC-89[3] stretch paint (aliphatic polyurethane gloss paint) and Skin-Flex SC-89 thinner[4] to create a first substrate having a thickness of from about 100 μm to about 600 μm, and allow to dry for at least 12 hours. A substrate material[5] may then be poured into the second negative mold (onto the gloss paint, if present) in an amount sufficient to produce a substrate having a thickness of approximately 0.1 mm-1 cm.

[1] Suitable materials include PLY-O-LIFE™ and ALGIFORM™ casting material, both available from Pink House Studios (St. Albans, Vt.); or other suitable equivalent materials.
[2] Other suitable materials include dental materials, liquid rubber, room temperature vulcanized (RTV) rubber, plastic, or equivalents thereof.
[3] SC-89 Stretch Paint, available from Burman Industries (Van Nuys, Calif.).
[4] SC-89 Thinner, available from Burman Industries, (Van Nuys, Calif.).
[5] TC-410 polyurethane, Part A (aromatic diisocyanate based pre-polymer, plasticizer mixture) and Part B, polyurethane curing agent, for example, polyether polyol, di(2-ethylhexyl) adipate, aromatic amines, aryl mercuric carboxylate) with Parts A and B in a 1:1 ratio. Optionally, Part C (Plasticizer-ester) may be included at a level of 1% to 150% by weight of the combination of Parts A and B. An acceptable alternative to TC-410 parts A and B is Skin Flex, Part A (aromatic diisocyanate terminated polyoxypropylene glycol mixture); Part B, polyurethane curing agent (polyol-diamine mixture), with Part A and Part B in a 1:2 ratio; and optionally Skin Flex Part C (Plasticizer-ester) at a level of 1% to 150% by weight of the combination of Parts A and B; all available from BJB Industries (Tustin, Calif.).

Example 2

The following illustrates one example of the process for making a suitable substrate:

Combine equal amounts of Part A and Part B of TC-410 polyurethane, or equivalent materials, and thoroughly mix. Slowly pour a sufficient amount of the mixture into a desired mold, starting from the edge and gradually moving to the center of the mold. The amount should be sufficient to produce a substrate having a thickness of approximately 0.1 mm-1 cm. One example of a suitable amount is 25 ml in a mold having an area of 7 cm×14 cm. Allow to cure overnight. Begin peeling the polymer substrate from the mold, starting from the edge. Cut away the border if necessary. When poured into a mold as described in Example 1, the substrate thus made has the texture of human keratinous tissue of the body part used to make the first negative imprint.

Example 3

The following example illustrates a process of directly imparting a texture to a substrate surface.

A patterned surface resembling the surface of mammalian keratinous tissue, for example forearm skin, or hair, may be mechanically etched onto a metallic surface, following standard procedures of photolithography known to one of skill in the art. First, create a pattern that resembles the texture of human skin, for example, from the forearm, either as a computer-simulated image, or as an actual image (e.g. photographic, microscopic) from the human body part of interest. Transfer the pattern to a clear sheet to form a mask. Place the mask onto a copper, brass or other appropriate metallic sheet, upon which a photoresist has been previously adhered or laminated. A variety of photoresists are available commercially, for example DuPont™ MX series dry film photoresists. The selection of the photoresist is based on the desired size, texture and/or feature of the keratinous tissue-texture. Expose the composite of metal/photoresist/mask to an appropriate dose of UV light, using industry standard exposure tools. Remove the mask, develop the photoresist and etch the metal layer using appropriate etching solutions, as described in standard textbooks on second level microelectronics packaging.[1]

[1] Donald Seraphim, Ronald Lasky and Che-Yu Li: "Principles of Electronic Packaging," Mc-Graw Hill Inc. (1989).

Pour a 1:1 mixture of Skin-Flex SC-89 Stretch-paint and Skin-Flex SC-89 Thinner, as described in the previous examples, into the metallic mold and allowed to dry overnight. Adjust the amount of poured mixture, according to the size of the mold, to yield a final substrate that is typically between 600 to 800 micrometers thick. After overnight drying, the substrate material is carefully peeled off of the metallic mold as described above. The substrate material may be surface-modified, or fixedly coated, to impart more specific skin surface properties.

Example 4

The following example illustrates one process for stably affixing a suitable coating material to a substrate by means of plasma coating.

Plasma deposition may be performed in a plasma unit consisting of a cylindrical vacuum chamber having a diameter of approximately 30.5 cm and a length of 61.0 cm. Vacuum may be produced by means of a Leybold PCS 25 vacuum pump. The RF energy may be supplied from a PE 1000 Advanced Energy 40 KHz power supply, across a set of parallel A1-electrodes in the vacuum chamber. Create plasma in the vacuum chamber, between the two electrodes, by application of the RF power. The effective plasma treatment area is approximately 40 cm by 20 cm.

Plasma deposition may be achieved through the following process: Place the substrate material (sample) on a perforated aluminum sample tray in between parallel plate aluminum electrodes in the plasma chamber. Reduce the chamber base pressure to approximately 100 milliTorr (mTorr). Allow a mixture of argon and nitrogen gas, at flow rates of 20 sccm of Ar and 10 sccm of nitrogen, (where "sccm" means standard cubic centimeter per minute) to flow into the chamber for about one hour to substantially degas the sample to be coated. Reduce the base pressure to 10 mTorr, and 25 W continuous wave RF power is applied for approximately 5 minutes while allowing the argon/nitrogen mixture to flow into the chamber at the same flow rates. Stop the Ar and N2 flow, evacuate the chamber again to 10 mTorr, and introduce the coating material[1] (monomer) into the chamber to a pressure of 100 mTorr, selecting a flow rate of about 10 sccm to 200 sccm. The rate will depending upon the monomer used and will be within the knowledge of or may be determined with limited experimentation by one of skill in the art. Apply a continuous wave radiofrequency (RF) power at 25 W for 25 minutes while maintaining a vapor pressure of approximately 100-120 mTorr. This results in the deposition of the monomer onto the sample surface in the form of a polymeric coating that is covalently bonded to the sample surface. Instead of 25 W continuous power, RF power may be applied in the pulsed mode, with on/off time ratios of 1 to 1000, and on times in the range of 10 microseconds to 1 sec, to fine-tune the chemical nature of the coating on the sample surface. The exact times will be within the knowledge or may be determined with limited experimentation by one of skill in the art. Power source can also be varied between microwave (MW) and RF, with frequencies selected from available and allowed ranges for MW or RF sources. Turn the power off, and stop the flow of the coating material. Purge the chamber with about 20 sccm Ar for about 30 min. Remove the plasma coated surfaces from the chamber and determine the contact angle, surface charge and the thickness of the coating layer determined by video contact angle measurement system (VCA-2500 from ASM), zeta-potential measurement (Anton Parr Electrokinetic Analyzer, Model BI-EKA) and Atomic Force Microscopy (Q-Scope 250 from Quesant Corporation) methods. The plasma coating process can be performed with more than one monomer, used either together to form a combination coating with polymeric species generated from both monomers simultaneously, or as separate coating layers resulting from each monomer applied separately and sequentially.

02-2 (available from Avocado Chemicals). However, one of skill in the art will understand that a variety of coating materials, as described herein, may be used, the choice of which will be determined by the surface property of the keratinous tissue that one desires to reproduce.

[1] Suitable coating materials include allylamine (98%, $C_3H_7N$, available from Aldrich, CAS 107-11-9); 1,1,1-trimethyl-1-pentene; 2,4,4-trimethyl-1-pentene (both available from Aldrich); allyl alchol ($C_3H_6O$, CAS 107-18-6, from Aldrich ); and perfluoromethylcyclohexane monomer ( $C_6F_{11}CF_3$, CAS 355-

The following chart summarizes measurements performed as described herein on various substrates.

| Substrate | Dispersive Component of Total Surface Energy (mJ/m$^2$) | Polar Component of Total Surface Energy (mJ/m$^2$) | Total Surface Energy (mJ/m$^2$) | Zeta-Potential (mV)[1] | Contact Angle in degrees (H2O) | Contact Angle in degrees (Diiodo-methane) | Contact Angle in degrees (ethylene glycol) | Stable |
|---|---|---|---|---|---|---|---|---|
| Normal Skin[2] | 30.30 | 0.20 | 30.50 | | | | | N/A |
| Winter Skin[3] | 29.50 | 0.06 | 29.60 | | | | | N/A |
| Summer Skin[4] | 29.70 | 3.10 | 32.80 | | | | | |
| Wet Skin[5] | 25.85 | 11.31 | 37.16 | | | | | N/A |
| Scalp[6] | 29.30 | 12.70 | 42.00 | | | | | N/A |
| Lips[7] | 33.00 | 5.50 | 38.50 | | | | | N/A |
| Bicomponent polyurethane (TC-410)[8] | 47.31 | 2 | 49.31 | (−) 22 | | | | Yes[20] |
| Polyurethane substrate with allyl amine coating layer[9] | 32 ± 1.5 | 12 ± 1.5 | 45 ± 1.0 | (+) 8.4 | 65 ± 2 | 41 ± 2 | 33 ± 1.0 | Yes[20] |
| Polyurethane substrate with plasma deposited allyl alcohol coating layer[10] | 28.9 | 12.6 | 41.45 | (−) 7.1 (−) 15.2 | | | | Yes[20] |
| Polyurethane substrate plasma deposited with 1,1,1-trimethyl-1-pentene coating layer[11] | 31 ± 1 | 0.5 ± 0.3 | 32 ± 1.0 | (−) 27.4 | 100 ± 2.0 | 48 ± 2.0 | 67 ± 1.0 | Yes[20] |
| Polyurethane substrate plasma deposited with PFMCH coating layer.[12] | 19 ± 2.0 | 0.6 ± 0.2 | 20 ± 1.0 | (−) 37.1 | 110 ± 2 | 82 ± 2.0 | 92 ± 2.0 | Yes[20] |
| Comparative Examples | | | | | | | | |
| VITRO SKIN[13] | 31.55 | 8.52 | 40.07 | | | | | No[16] |
| COFFI film[14] | 28.06 | 9.12 | 37.17 | | | | | No[17] |
| BIOSKIN[15] (Black) | 44.5 | 16.2 | 60.6 | | 46.1 ± 2.6 | 29.4 ± 2.2 | | No[18] |
| BIOSKIN[15] (Brown) | 31.0 | 1.36 | 32.36 | | 89.8 ± 0.3 | 55.7 ± 0.2 | | No[19] |

[1] measured at a pH of about 5.0.

[2] skin from forearm. Measurements may be made as follows: Shave any hair from skin 2-3 days prior to measurement. Place a drop of desired liquid on the skin, which is positioned horizontally. Capture the contact of the drip with a high speed (e.g. at 0.017 seconds per image) video stream for about 3 seconds. Use suitable software to non-spherically trace the droplets and determine the contact angle, e.g. First Ten Angstroms ™ Model 200 Dynamic Contact Angle Analyzer. Calculate the mean contact angle for both sides of the drop.

[3] "winter" skin measurement made as described in [2], at a temperature of approximately 0° C., a dew point of approximately −4° C. and a relative humidity of approximately 70%.

[4] "summer" skin measurement made as described in [2], at a temperature of approximately 24° C., a dew point of approximately 18° C. and a relative humidity of approximately 55%.

[5] wet skin measurement made after immersion in distilled water for about 5 min. while still immersed. Solvents used to determine contact angles under water were bromonaphthalene, diiodomethane, and hexane. Contact angles converted into surface energy by Augustine Scientific, Cleveland, OH.

[6] scalp measurements made as described in [2].

[7] lip measurements made as described in [2].

[8] See examples 1 and 2.

[9] Bicomponent polyurethane with plasma-deposited allyl amine coating layer. Plasma deposition performed using pulsed deposition, as described in Example 4, using 25 W continuous wave deposition at 40 KHz power.

[10] Bicomponent polyurethane with plasma-deposited allyl alcohol coating layer. Plasma deposition performed using 7 W continuous wave deposition as described in Example 4.

[11] Bicomponent polyurethane with plasma-deposited 1,1,1-trimethyl-1-pentene coating layer. Plasma deposition performed using continuous wave deposition at 25 W and 40 Khz power.

[12] Bicomponent polyurethane with plasma-deposited PFMCH coating layer. Plasma deposition performed using continuous wave deposition at 25 W and 40 Khz power.

[13] IMS Inc., Orange, CT

[14] distributed by Brechteen, Chesterfield, MI

[15] Beaulax Co., Ltd., Tokyo, Japan

[16] Upon wetting, loss of texture renders substrate unsuitable for re-use as described herein.

[17] Substrate exhibited swelling and loss of texture after one use.

[18] Substrate exhibited loss of texture upon cleaning with solvents such as neat ethanol.

[19] Substrate delaminates, i.e. laminated coating layer is removed, upon rubbing with solvents such as neat ethanol.

[20] Substrate retains texture and coating layer after multiple uses and cleanings, and is stable as defined herein.

Example 5

The following example illustrates one non-limiting method of using the article of manufacture of the present invention to measure the benefit of a product.

Prepare a coating substrate having properties similar to wet skin as described above. Weigh the dry surface, and analyze the surface by scanning electron microscopy (SEM). Pre-heat the coated substrate to normal human body temperature. Topically apply an in-shower moisturizer to the coated substrate, and rinse the substrate with running water for about 5 minutes. Allow the surface to dry and weigh the surface. An increase in mass of the coated substrate provides an indication of how effectively the product adheres to the coated substrate, and how effectively the product would adhere to human skin under similar conditions. The SEM images provide evidence of how effectively the product coats the textured surface.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of evaluating the interaction of at least one consumer product with mammalian keratinous tissue, comprising the steps of:
   (1) topically applying at least one said consumer product to a coated surface of an article of manufacture comprising:
   a) a substrate comprising a polymer;
   b) a coating layer comprising a plasma-deposited coating material selected from the group consisting of allyl amine, allyl alcohol, 1,1,1-trimethyl-1-pentene, 2,4,4-trimethyl-1-pentene, perfluoromethylcyclohexane monomer, and combinations thereof, wherein:
   i) said coating layer is stably affixed to said substrate to form a stable, coated surface, wherein said coated surface has a texture that mimics the topography of mammalian keratinous tissue; and
   ii) said coated surface demonstrates at least one physical property representative of mammalian keratinous tissue, selected from the group consisting of a total surface energy of from about 15 $mJ/m^2$ to about 50 $mJ/m^2$, a dispersive component of the surface energy of from about 15 $mJ/m^2$ to about 50 $mJ/m^2$, a polar component of the total surface energy of from about 1 $mJ/m^2$ to about 14 $mJ/m^2$, a zeta-potential at a pH of about 5.0 of from about −40 mV to about 30 mV, and combinations thereof; and
   (2) measuring the interaction of said consumer product with said coated surface.

2. The method of claim 1, wherein said consumer product is a skin care product.

3. The method of claim 1, wherein said consumer product is a hair care product.

4. The method of claim 1, wherein said consumer product is a fabric care product.

5. The method of claim 1, wherein said consumer product is an adhesive product.

6. The method of claim 1, wherein said consumer product is an active ingredient.

7. The method of claim 1, wherein said consumer product is an absorbent product.

8. The method of claim 1, wherein said consumer product is selected from the group consisting of moisturizers, cleansers, cosmetics, shampoos, conditioners, styling agents, hair bleaches, hair colorants, deodorants, antiperspirants, perfumes, and combinations thereof.

9. The method of claim 1, wherein said consumer product is selected from the group consisting of fabric softeners, fabric detergents, fabric cleansers, fabric whiteners and fabric deodorizers.

10. The method of claim 1, wherein said consumer product is selected from the group consisting of facial tissue, toilet tissue, paper towels, catamenial pads, tampons, diapers, wipes, adult incontinence products, and combinations thereof.

* * * * *